United States Patent [19]

Mericle

[11] Patent Number: 4,527,562
[45] Date of Patent: Jul. 9, 1985

[54] NON-METALLIC, BIO-COMPATIBLE HEMOSTATIC CLIPS

[75] Inventor: Robert W. Mericle, Lebanon, N.J.

[73] Assignee: Ethicon, Inc., Somerville, N.J.

[21] Appl. No.: 468,518

[22] Filed: Apr. 5, 1983

Related U.S. Application Data

[63] Continuation-in-part of Ser. No. 276,131, Jun. 22, 1981, abandoned, which is a continuation-in-part of Ser. No. 49,379, Jun. 18, 1979, abandoned.

[51] Int. Cl.³ .................. A61B 17/12; A61B 17/00
[52] U.S. Cl. ...................................... 128/325; 128/346
[58] Field of Search .................. 128/325, 326, 346

[56] References Cited

U.S. PATENT DOCUMENTS

| | | | |
|---|---|---|---|
| 4,325,377 | 4/1982 | Boebel | 128/326 |
| 4,361,229 | 11/1982 | Mericle | 128/325 |
| 4,418,694 | 12/1983 | Beroff et al. | 128/346 |
| 4,424,810 | 1/1984 | Jewusiak | 128/346 |
| 4,425,915 | 1/1984 | Ivanov | 128/325 |
| 4,434,795 | 3/1984 | Mericle | 128/346 |
| 4,446,865 | 5/1984 | Jewusiak | 128/346 |
| 4,449,531 | 5/1984 | Cerwin et al. | 128/346 |
| 4,450,839 | 5/1984 | Transue | 128/325 |

Primary Examiner—C. Fred Rosenbaum
Assistant Examiner—C. W. Shedd
Attorney, Agent, or Firm—Robert L. Minier

[57] ABSTRACT

A sterile hemostatic clip made from polymeric materials having a pair of leg members connected by a resilient hinge. The distal ends of the leg members terminate in latch means. The outer surface of each leg member carries a suitable boss to allow the clip to be held and placed about a vessel to close the vessel utilizing a suitable instrument.

7 Claims, 5 Drawing Figures

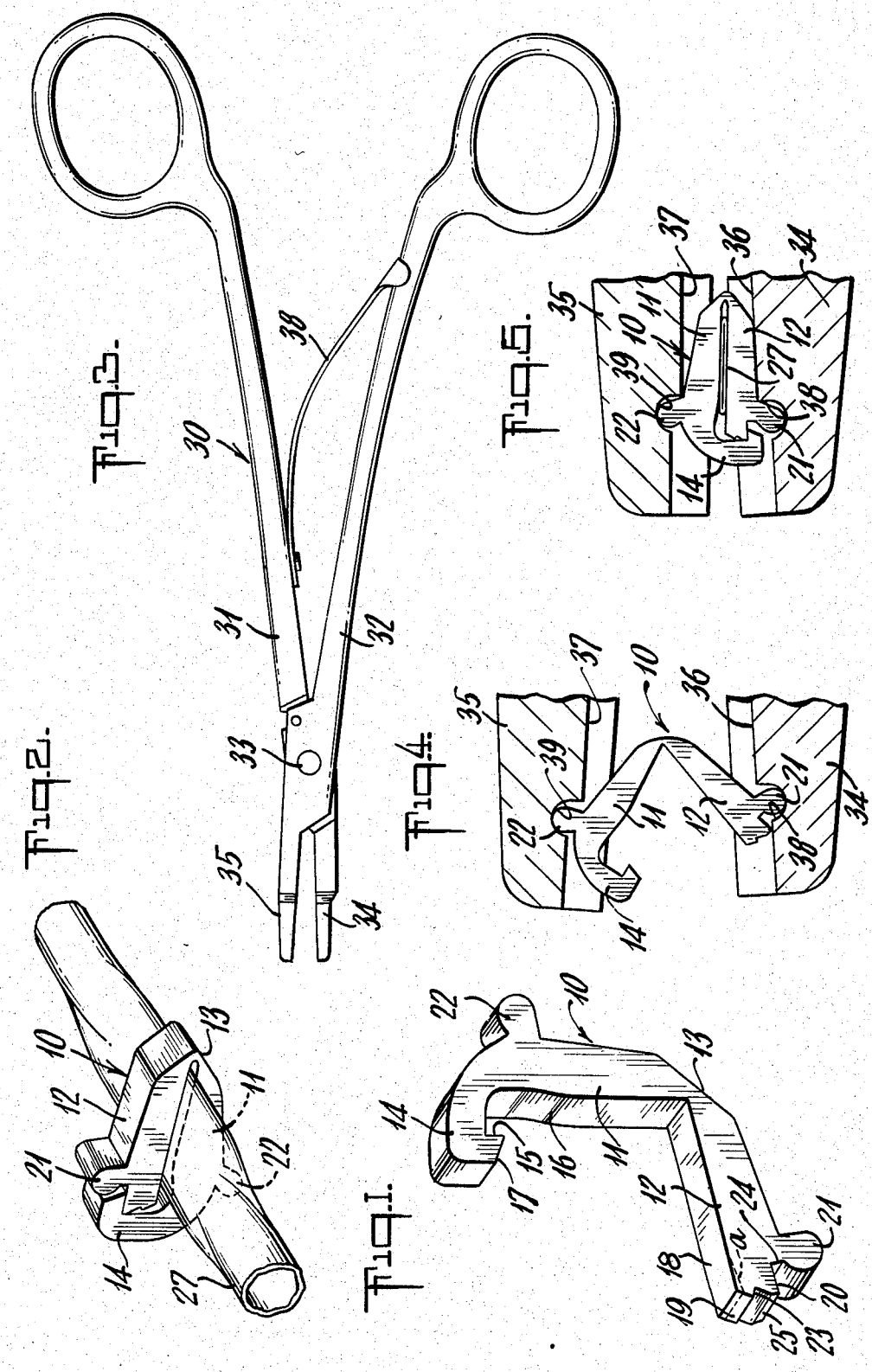

NON-METALLIC, BIO-COMPATIBLE HEMOSTATIC CLIPS

The present application is a continuation-in-part application of co-pending application Ser. No. 276,131 filed June 22, 1981, now abandoned which in turn was a continuation-in-part application of co-pending application Ser. No. 49,379, filed June 18, 1979, also now abandoned.

The present invention relates to hemostatic clips and clip appliers, and, more particularly, to hemostatic clips fabricated from absorbable or non-absorbable polymeric materials and to instruments for applying such clips to blood vessels and the like.

BACKGROUND OF THE INVENTION

In many surgical procedures, it is often necessary to ligate a plurality of vessels within the surgical site. The vessels may then be severed downstream of the ligated portion. In some instances, the vessel may be ligated at two spaced apart areas and the portion of the vessel between the ligations removed. The primary reason for ligating the vessels is to maintain the surgical site free of an excess of blood and to reduce blood loss in the patient. Also in certain surgical procedures wherein tumors or parts of organs and the like are to be removed, the tumor or organ may have to be separated from certain vessels and before separating the vessels will have to be ligated.

Once a blood vessel is completely shut off, hemostasis; that is, the natural closing of the ligated end of the vessel so as to stop blood flow will occur in several days depending on the vessel. The body, in the meantime, will continue to allow blood to flow around the ligated area through appropriate capillaries and secondary vessels with the natural physiological functions of the body enlarging these by-pass vessels until adequate blood flow is attained. Hence, when ligating the vessel, there should be a positive stopping of the blood flow in the main vessel; i.e., no leakage, which might cause blood loss in the patient and may disrupt the natural hemostasis and concurrent manufacture of new paths of blood flow in the patient.

In the past, this closing of the vessel was usually accomplished using ligatures; i.e., threads or filaments which the surgeon tied around the vessel desired to be closed. A very time consuming process, and one in which positive closure of the vessel was not always accomplished.

In relatively recent years, hemostatic clips have replaced the ligatures in many surgical procedures to close blood vessels and other small fluid ducts. These hemostatic clips have been narrow U-shaped or V-shaped strips formed of tantalum or stainless steel which are capable of being deformed and possess sufficient strength to retain the deformation when clamped about a blood vessel. The clips are generally applied using a forceps-type device having jaws channeled or otherwise adapted to hold the open clip. Representative hemostatic clips and appliers of the prior art are best illustrated in U.S. Pat. Nos. 3,867,944; 3,631,707; 3,439,523; 3,439,522 3,363,628; 3,312,216; and 3,270,745.

Although the metal hemostatic clips are relatively easy to apply and accomplish a positive closing of the vessel, the metal devices are expensive to manufacture and perhaps more importantly disrupt post-operative X-ray procedures and future diagnostic imaging procedures. Hence, it is desired the hemostatic clips be made from materials which will not disrupt the post-operative or other subsequent diagnostic procedures, such as X-ray imaging, computerized axial tomography imaging, and the like.

It has been suggested in the prior art, as in U.S. Pat. No. 3,429,523, for example, that hemostatic clips might be formed of inexpensive plastics or materials which are slowly absorbable in the body. Unfortunately, conventional U-and V-shaped hemostatic clips do not possess the required strength or deformability when constructed of known plastic materials to be successfully clamped about a blood vessel. Thus, although the need and desirability of providing inexpensive plastic ligating clips of both absorbable and non-absorbable materials has been recognized for over ten years, there has been no practical way to satisfy this need.

To accomplish the positive closing of the vessel with non-metallic, bio-compatible hemostatic clips, the vessel clamping surfaces of the clips should have minimal or no gap between the surfaces when the clip is closed. Also, the surfaces should be sufficiently smooth and have large enough areas so as not to sever or even partially sever the closed vessel. The non-metallic, bio-compatible hemostatic clip, once placed in a clamping position on a vessel, must maintain that position for the period of time required for hemostasis to take place. The clip must maintain its strength in vivo to withstand the pressure trying to force the vessel back open for a sufficient period of time to allow for the natural permanent shutting of the vessel. Also, hemostatic clips should be sterilizable by the well known sterilizing techniques; such as, ethylene oxide treatment, cobalt irradiation, and the like.

The configuration of a hemostatic clip is also important. Because the clip is often used in and around the important organs of the body and the clip is left in the body after the surgical procedure is completed, it is important that the clip be configured to keep trauma within the area; i.e., irritation from a foreign object, to a minimum. Smoothness and size of the clip as well as a lack of projections and a minimum of sharp angles all contribute to reducing the trauma which may occur when placing a foreign object such as a hemostatic clip, within a human body.

The clip configuration is also important to insure the proper placement of a clip. When hemostatic clips are used in a surgical procedure the general practice is for the nurse to pick up a clip in the jaws of a forceps type applying instrument. The nurse passes the instrument with the clip in place to the surgeon. The surgeon places the jaws of the instrument into the surgical site and around the vessel to be ligated. In many instances, the surgeon will be placing the jaws of the instrument into areas where the surgeon has very limited vision. The surgeon then closes the clip over the vessel to the ligated. All of the handling and manipulation of the instrument must be accomplished without dropping the clip and while maintaining the sterility of the clips.

The size of the clip is also important as the smaller the clip, the less foreign material there is being implanted in the patient. Also, the smaller size allows for more clips to be used in a surgical procedure and in certain instances may simplify the procedure or at least reduce possible side effects resulting from the insertion of foreign objects within the human body.

U.S. Pat. No. 3,926,195 describes a plastic clip designed for the temporary or permanent closing of the oviduct and vas deferens in humans. These clips preferably have a clamping surface of from 6 to 10 mm in length and 3 to 6 mm in width. The size of such clips are accordingly considerably larger than is desirable for hemostatic clips. Additionally, clips of U.S. Pat. No. 3,926,195 require the use of several complex tools to apply the clips which are acceptable for the purposes described in the reference but would be unacceptable in a surgical procedure requiring the rapid placement of a large number of hemostatic clips to stem the flow of blood from severed vessels.

While the importance of the clip to the surgical procedure has been discussed, it should be pointed out that the configuration of the clip is also important to the manufacture of the clip. The configuration should be such as to take advantage of simple and economic means of manufacture of the clip such as injection molding. The configuration should be such as to reduce the production of seconds or malformed clips in the production. Also, the configuration of the clip should be such as to allow for very simple design of the jaws of the applier to reduce cost of the applier while maintaining the required assurance of holding and setting of the clip during the surgical proceedings.

It is accordingly an object of the present invention to provide a plastic hemostatic clip effective for clamping off small blood vessels and other fluid ducts in the body. It is a further object of this invention to provide plastic hemostatic clips of both absorbable and non-absorbable materials. It is yet a further object of this invention to provide plastic hemostatic clips which are quickly and easily applied to severed blood vessels and other fluid ducts with a single forceps-type instrument as commonly used in applying metallic clips.

SUMMARY OF THE INVENTION

The hemostatic clips of the present invention have good in vivo strength properties and have vessel clamping surfaces with minimal or no gap between the surfaces when the clip is in the closed position to provide positive clamping of vessels and, hence, attain the desired hemostasis within the period of time of from 3 to 5 days.

The hemostatic clips of the present invention are configured so as cause a minimum of trauma once implanted in a patient yet unexpectedly provide improved assurance that the clip will be handled and manipulated during the surgical procedure without being dropped or rendered unsterile. It is believed the symmetry in the outer surfaces of my new clip improves the handling and manipulative characteristics of my new clip.

Since the clips of the present invention are made from non-absorbable polymer materials such as nylon, polypropylene, or the like, or absorbable polymer materials, such as a homopolymer or copolymer of lactide and glycolide, dioxanone, or the like, they do not disrupt post-operative or other subsequent diagnostic procedures used on a patient such as X-ray imaging, CAT scanning, and the like. My new clips may be rendered sterile by any of the well-known sterilization procedures such as ethylene-oxide, cobalt irradiation, and the like, depending on the specific polymers used.

The size and configuration of my new clip provides that the total amount of material used in the manufacture of a clip is kept to a minimum. Reducing the amount of foreign matter implanted in the patient allows for the use of more clips when required in a surgical procedure, yet surprisingly even with this reduced amount of material used in each individual clip, my new clip maintains all of the desired in vivo properties described above.

The new clips of the present invention are formed in a normally open position and may be easily and economically produced and manufactured by injection molding or other suitable techniques with a minimum production of seconds or poor quality clips because of malformation in the clip configuration. I believe this is, at least in part, due to the symmetry present in my new clip configuration. Also, the instrument required to apply my new clips is of a simple design and requires no specific alignment between the jaws of the instrument and the clip other than to place the jaws of the instrument over the outer surfaces of the clip and remove the sterile clip from its sterile holder.

The hemostatic clip of the present invention comprises first and second leg members joined at their proximal ends by a simple, resilient hinge means and terminating at their distal ends in latch means.

The hinge section of the clip according to the present invention is resilient; i.e., elastic memory, and acts as a spring which assists in the packaging of the clip as well as in the handling and placement of the clip. This resilience allows for slight forces to be applied to the clip while it is being packaged in order to maintain the clip in a desired position within the package. This resilience also allows the clip to snap into the jaws of a suitable applying instrument and allows the jaws to be slightly flexed during handling of the instrument without the clip becoming dislodged. As can be appreciated, this is a considerable advantage when utilizing the clips of the present invention.

Each leg member has an outer surface and a vessel clamping inner face with the vessel clamping inner face being in opposition to a vessel clamping inner face of the other leg member. When the clip is in the closed position, there is minimal or no gap between the vessel clamping faces.

The first leg member terminates at its distal end in a portion of the latch means. This portion comprises a deflectable hook member extending from the inner face of said leg member. The hook member has an inner face spaced from the inner face of said leg member and substantially parallel thereto. The end face of the hook member is beveled so as to form an acute angle with the inner face of the hook member. The leg member has a boss disposed on its outer surface. The boss has a cylindrical shape with the axis of the cylinder extending across the width of the leg member. The boss is spaced from the proximal end of the leg member.

The second leg member terminates at its distal end in a complementary portion of the latch means. This portion comprises an end face of said leg member having a bevel complementary to the bevel on the end face of the hook member. The complementary bevel forms an obtuse angle with the inner face of the second leg member and is adapted to deflect the hook member and enter the space between the inner face of the hook member and the first leg member. The second leg member has a boss disposed on its outer surface. The boss has a cylindrical shape with the axis of the cylinder extending across the width of the leg member. The boss is spaced from the proximal end of the leg member.

When the first and second leg members are pivoted about the hinge means, the distal end of the second leg member deflects and engages the hook member of the first leg member to lock the clip in a closed position.

The applier for the clips of the present invention is a forceps-type instrument wherein each jaw is channeled to receive the width and length of the clip and a cylindrical recess is provided across the base of each channel to receive the boss on each leg of the clip. The depth of the channel in each jaw forward of the cylindrical recess (between the cylindrical recess and the tip of the jaw) is greater than to the rear of the cylindrical recess. When the open clip is placed between the jaws of the applier, it is held firmly in place with the boss of each leg in the recess of each jaw. As the jaws are closed, the boss of each leg rotates in the recess of the jaw until the distal end of the second leg bypasses and locks under the hook member of the first leg.

DESCRIPTION OF DRAWINGS

FIG. 1 is a greatly enlarged view in perspective of a hemostatic clip according to the present invention.

FIG. 2 illustrates the clip of FIG. 1 clamped about a blood vessel.

FIG. 3 illustrates a forceps-type applier useful with the clips of the present invention.

FIG. 4 illustrates the open clip of FIG. 1 retained in the jaws of a forceps-type clip applier.

FIG. 5 illustrates the clip of FIG. 4 closed and locked over a blood vessel in the jaws of the applier.

DESCRIPTION OF PREFERRED EMBODIMENTS

Referring now to FIG. 1, there is illustrated hemostatic clip 10 constructed of two leg segments 11 and 12 connected at the proximal ends thereof by hinge section 13. Leg 11 terminates at the distal end thereof in hook member 14 having inner face 15 substantially parallel to inner face 16 of leg 11 and forming an acute angle with end face 17. Leg member 12 terminates at the distal end in end face 19 which forms an obtuse angle with inner face 18 of leg 12. End face 19 is offset at 23 to form a notch approximately midway between surfaces 18 and 20, and additionally is squared off at face 25 to form a substantially right angle with surface 20.

The length and width of faces 16 and 18 are substantially equal, and face 15 of hook 14 is spaced from face 16 of leg 11 by a distance corresponding to the thickness of leg 12 between the plane of face 18 and surface 20. When legs 11 and 12 are pivoted about hinge 13 to bring faces 18 and 16 into opposition, hook 14 is deflected by surface 19 of leg 12 until the distal end of leg 12 snaps under hook 14 and is thereby locked in place. End face 17 of hook 14 and end face 19 of leg 12 are angled as illustrated to facilitate the passage of leg 12 past hook 14 during clip closure.

When the clip is closed over a tubular vessel as illustrated in FIG. 2, surfaces 16 and 18 engage and compress vessel 27 to close the lumen thereof. Surfaces 16 and 18 may be smooth as illustrated in FIG. 1, or may be provided with ridges or grooves to increase vessel holding power. Leg 11 may also be undercut at the juncture of hook member 14 and surface 16 as illustrated at 26 in FIG. 1 to allow for overtravel and to increase the deflectability of hook member 14 and increase the space between the hook member 14 and leg 11, thereby compensating for any inward deflection of hook 14 during closure which might reduce the clearance between surfaces 15 and 16 and otherwise interfere with the latching of the clip.

Referring again to FIG. 1, leg 12 of clip 10 includes an outside cylindrical boss 21 with the axis of the cylinder extending across the width of the leg near the distal end thereof. Boss 21 is spaced from surface 25 a distance sufficient to permit full engagement of hook member 14 by leg 12 when the clip is in a closed and latched position. Cylindrical bosses 21 and 22 are equidistant from hinge means 13 so that when the clip is closed, bosses 21 and 22 define a line perpendicular to the major axis along the length of the clip as best illustrated in FIG. 5. Leg segments 11 and 12 are identical in cross-section from the hinge up to the bosses. This configuration equalizes the bending forces of the leg segments when clamped about a blood vessel.

The distal end of leg 12 forward of lug 21 is of reduced thickness relative to the thickness immediately to the rear of lug 21. A step or notch 24 is disposed between lug 21 and surface 20.

One purpose for this notch 24 is to aid in holding the clip in the jaws of an appropriate clip applying instrument. The notched portion may be provided on one or both cylindrical bosses as desired. The notch may be positioned at the other places on the surface of the boss to aid in holding the clip in the jaws of the instrument.

When closing the clip shown in FIG. 1 using a suitable clip applying instrument, the forces applied tend to push the clip forward out of the jaws of the instrument. By configuring the jaws of the instrument so it engages the notch shown in FIG. 1, the forward forces placed on the clip as the clip is closed are counteracted.

The clip configuration will be more fully appreciated in connection with the instrument used to apply and close the clip as illustrated in FIGS. 3 through 5.

FIG. 3 illustrates a forceps-type ligating clip applier 30 comprising two handle members 31 and 32 crossing at hinge point 33 and maintained in a normally open position by spring 38. Handle 31 extends beyond hinge 33 forming jaw member 34 while the extension of handle 32 forms jaw member 35.

FIG. 4 illustrates the detail of the construction of jaws 34 and 35 and the interaction of the jaws with the clip of FIG. 1. Jaws 34 and 35 are of identical design and are provided respectively with channels 36 and 37 extending rearwardly from the tips of the jaws. Each channel is provided with a cylindrical recess 38 and 39 respectively across the width of the channel and near the distal end thereof. Recesses 38 and 39 are in alignment when the jaws of the applier are closed and are sized to receive the cylindrical lugs 21 and 22 of the clip. Channels 36 and 37 forward of recesses 38 and 39 are deeper than to the rear of the recesses as illustrated in FIG. 4. When the open clip is held in the applier, the cylindrical lugs on the clip extend into the cylindrical recesses in each jaw. Due to the angle of the clip in the applier, the distal ends of legs 11 and 12 extend into the deeper forward channel section of each jaw. The reduced thickness of leg 12 at the distal tip prevents interference between the tip and the channel of the applier when the clip is held in the slightly closed position as illustrated in FIG. 4. The resilience or elastic memory of the hinge retains the clip firmly in the recesses of the applier.

Clip 10 is initially loaded in applier 30 in the position as illustrated in FIG. 4. When locking the clip in the applier, the bosses provide an audible click and a tactile response when the clip snaps into the recesses of the applier. These properties allow the user to know when he has a properly loaded clip in the applier. After moving the jaws of the applier and the clip into position over the vessel to be ligated, the jaws of the applier are closed and the clip is locked in position over the vessel as illustrated in FIG. 5. As the clip is closed, the cylindrical lugs of legs 11 and 12 rotate, journal-like in the cylindrical recesses of jaws 37 and 36 until the outer surfaces of legs 11 and 12 rest on the corners 40 and 41 of channel 36 as illustrated in FIG. 5. At this point, the distal end of leg 12 has rotated away from the base of the channel and sufficient space exists for hook 14 to bypass leg 12 and latch over the outer surface thereof. After the clip has been securely latched over the vessel to be ligated, the jaws of the applier are opened to release the clip and vessel and a new clip is loaded in the applier. Since the jaws of the applier, and clip pick-up features are identical, it is not necessary to orient the applier to the clip when loading the applier.

Many variations in the clip design other than the embodiments disclosed herein will be apparent to those skilled in the art and are contemplated within the scope of the present invention. For example, the undercut 26 at the juncture of hook 14 and surface 16 of leg 11 may be omitted, and the inner surface of leg 12 may be beveled at the distal end as indicated by broken line a in FIG. 1 to compensate for downward deflection of hook 14 during closure which might reduce the clearance under face 15 and interfere with the latching of leg 12. Offset 23 in end face 19 of leg 12 provides an intermediate latching position and effectively increases the length of face 18 at the distal end of leg 12, but may be omitted if desired. These and other modifications in the configuration of the clip may be employed without departing from the spirit and scope of the present invention.

The clips of the present invention may be constructed in various sizes according to their intended function. Hemostatic clips are typically less than 6 mm in length, about 1.5 mm in width, and have a vessel clamping surface about 3 mm in length. The dimensions of the clip may be reduced by about 50 percent for certain applications in microsurgery. Larger clips for special hemostatic applications and other functions such as closure of oviducts or vas deferens may have dimensions of about double those of a typical hemostatic clip. The various sizes of clips are preferably matched with individual appliers having jaws tailored to the size of the clip for best performance.

The clips of the present invention are most conveniently molded of biologically acceptable plastic materials which may be absorbable or nonabsorbable. Preferred absorbable polymers include homopolymers and copolymers of glycolide and lactide, and dioxanone. Preferred nonabsorbable polymers include nylon, polyester and polypropylene. All these materials have been demonstrated to be biologically acceptable when used as sutures or other implantable medical devices. The clips may also be cast or machined from solid polymeric materials.

Having now described the present invention and certain specific embodiments thereof it will be readily apparent to one skilled in the art that many variations and modifications may be made to the present invention without departing from the spirit and scope thereof.

What is claimed is:

1. A sterile hemostatic clip made from abosorable or nonabsorbable polymeric materials for application using a clip-applying instrument, said instrument having a pair of jaws for holding and placing said clip about the vessel to be ligated and for closing said clip to ligate said vessel, said clip comprising first and second leg members joined at their proximal ends by resilient hinge means and terminating at their distal ends in latch means, each leg member having an outer surface and a vessel clamping inner face, said vessel clamping inner face being in opposition to a vessel clamping inner face of the other leg member;

said first leg member terminating at the distal end thereof in a Portion of the latch means, said portion comprising a deflectable hook member extending from the inner face of said leg member, said hook member having an inner face spaced from the inner face of said leg member and substantially parallel thereto, the end face of said hook member being beveled so as to form an acute angle with the inner face of said hook member, said leg member having a boss disposed on a portion of its outer surface opposite the vessel clamping inner face, said boss having a substantially cylindrical shape with the axis of the cylinder extending across the width of the leg member, said boss adapted to rotably fit into a first jaw of the clip applying instrument and be held therein while the clip is being closed, said boss being spaced between the proximal and distal ends of the leg member;

said second leg member terminating at the distal end thereof in a complementary portion of the latch means, said portion comprising an end face of said leg member having a second bevel of supplementary angle to said acute angle on the end face of said hook member, said second bevel forming an obtuse angle with the inner face of said second leg member and adapted to deflect said hook member, said second leg member adapted to enter the space between the inner face of said hook member and the inner face of said first leg member with the end face of said leg member being enclosed by said hook member, said second leg member having a boss disposed on a portion of its outer surface opposite the vessel clamping inner face, said boss having a substantially cylindrical shape with the axis of the cylinder extending across the width of the leg member, said boss adapted to rotably fit into the second jaw of the clip applying instrument and be held therein while the clip is being closed, said boss being positioned so as to be substantially in opposition to said boss on said first leg member when said clip is closed;

whereby when the pair of jaws of the clip applying instrument having a clip therein are closed, the bosses of said clip rotate within the jaws of the instrument to allow said first and second leg members to pivot about said hinge means and the distal end of the said second leg member to deflect and engage the hook member of the first leg member to lock the clip in a closed position and on subsequent opening of the jaws the clip is released therefrom.

2. The hemostatic clip of claim 1 wherein the ends of the cylindrical shaped bosses on the first and second leg members are copolanar with the sides of their respective leg members.

3. The hemostatic clip of claim 1 or 2 wherein the raised cylindrical boss of said second leg member is spaced from the distal end of said second leg member by a distance corresponding to at least the length of the inner surface of said hook member.

4. The hemostatic clip of claim 1 or 2 wherein the thickness of the latch means of said second leg member is less than the thickness of said second leg member.

5. The hemostatic clip of claim 1 or 2 wherein said first leg member inner face is undercut proximate the juncture of said hook member and said inner face.

6. The hemostatic clip of claim 1 or 2 wherein there is a notch in said outer surface of at least one leg member between the associated cylindrical boss and latch means to aid in holding the clip in the jaws of the clip-applying instrument.

7. The hemostatic clip of claim 6 wherein the thickness of the latch means of said second leg member is less than the thickness of said second leg member and wherein said notch is contiguous to both the cylindrical boss and the latch means on the same of at least one leg member so as to prevent said clip from slipping toward the distal end of said jaws when being closed therebetween.

* * * * *